United States Patent [19]

Yasunami et al.

[11] Patent Number: 4,912,134
[45] Date of Patent: * Mar. 27, 1990

[54] AZULENE DERIVATIVES AND PHARMACEUTICAL COMPOSITIONS CONTAINING THEM

[75] Inventors: Masabumi Yasunami; Kahei Takase, both of Sendai; Takashi Meguro, Zushi; Katsumi Suzuki, Kawasaki; Osamu Hiwatashi, Kawasaki; Masaru Okutsu, Kawasaki; Nobuo Kato, Kawasaki; Toru Nakamura, Kawasaki, all of Japan

[73] Assignee: Ajinomoto Company, Inc., Tokyo, Japan

[*] Notice: The portion of the term of this patent subsequent to Aug. 22, 2006 has been disclaimed.

[21] Appl. No.: 166,481

[22] Filed: Mar. 10, 1988

Related U.S. Application Data

[63] Continuation-in-part of Ser. No. 117,539, Nov. 6, 1987, Pat. No. 4,859,701.

[30] Foreign Application Priority Data

Nov. 7, 1986 [JP] Japan .................. 61-264933

[51] Int. Cl.⁴ ...................... A61K 31/215; C07C 69/74
[52] U.S. Cl. ................................. 514/510; 549/305; 558/33; 560/119; 562/501; 568/303; 568/348
[58] Field of Search .................. 560/119; 514/510

[56] References Cited

FOREIGN PATENT DOCUMENTS 60-156611  8/1985  Japan .

OTHER PUBLICATIONS

43rd Annual Meeting of the Chemical Society of Japan, Mar. 1981, in Tokyo, Japan, Abstract II P889 with English translation.
The Tohoku Local Meeting of the Chemical Society of Japan in Fukushima, Japan, Oct. 2, 3, 1981, with English translation.

Primary Examiner—Michael L. Shippen
Attorney, Agent, or Firm—Oblon, Spivak, McClelland, Maier & Neustadt

[57] ABSTRACT

Azulene derivatives of the following formula

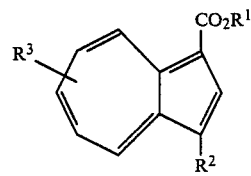

wherein $R^1$ stands for an alkyl group of 1 to 3 carbon atoms, $R^2$ stands for an alkyl group of 1 to 3 carbon atoms, and $R^3$ is at the 5- or 6-position and stands for an alkyl group of 1 to 6 carbon atoms, an aryl group of 6 to 9 carbon atoms or an aralkyl group of 7 to 10 carbon atoms; have antihyperlipidemic activity. Many of the compounds are also novel per se.

5 Claims, No Drawings

AZULENE DERIVATIVES AND PHARMACEUTICAL COMPOSITIONS CONTAINING THEM

The present application is a continuation-in-part of U.S. Ser. No. 117,539, filed Nov. 6, 1987, which is now U.S. Pat. No. 4,859,701.

FIELD OF THE INVENTION

The invention relates to novel azulene derivatives and to hypolipidemic agents comprising an azulene derivative as an effective ingredient.

BACKGROUND AND PRIOR ART

Hyperlipidemia is thought to be one of the causes for diseases such as hypertension, arteriosclerosis, and myocardial infarction. Certain azulene derivatives capable of being used as a hypolipidemic agent are already known, for example, 1-methoxycarbonyl-3-ethyl-7-isopropylazulene (JP-A-156611/1985) and certain formyl-substituted azulenes (EP 182491). Also, 6-isopropyl azulene 1-carboxylic acid methyl esters are known as intermediates in preparing 1,4-dimethyl-6-isopropyl azulene (Miyoshi et al, 43rd Ann. Meeting, Chem. Soc. of Japan, 1981, Abstract II p. 889), but not for any pharmaceutical use.

SUMMARY OF THE INVENTION

The present invention provides for pharmaceutical use, and especially hypolipidemic use, azulene derivatives shown by the following general formula:

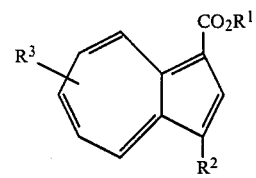

wherein: $R^1$ and $R^2$ are independently an alkyl group of 1 to 3 carbon atoms, such as methyl and ethyl, and $R^3$ is an alkyl group of 1 to 6 carbon atoms, such as methyl, ethyl, isopropyl, n-propyl, n-butyl, t-butyl, n-pentyl and isopentyl, an aryl group of 6 to 9 carbon atoms such as phenyl, tolyl and p-methoxyphenyl, or an aralkyl group of 7 to 10 carbon atoms such as benzyl and cinnamyl.

The invention also provides such azulenes as novel compounds per se, with the exception of the 6-isopropyl azulene 1-carboxylic acid methyl ester noted earlier.

DESCRIPTION OF PREFERRED EMBODIMENTS

The azulene derivatives of the present invention can be produced, for example, as shown in the reaction scheme below:

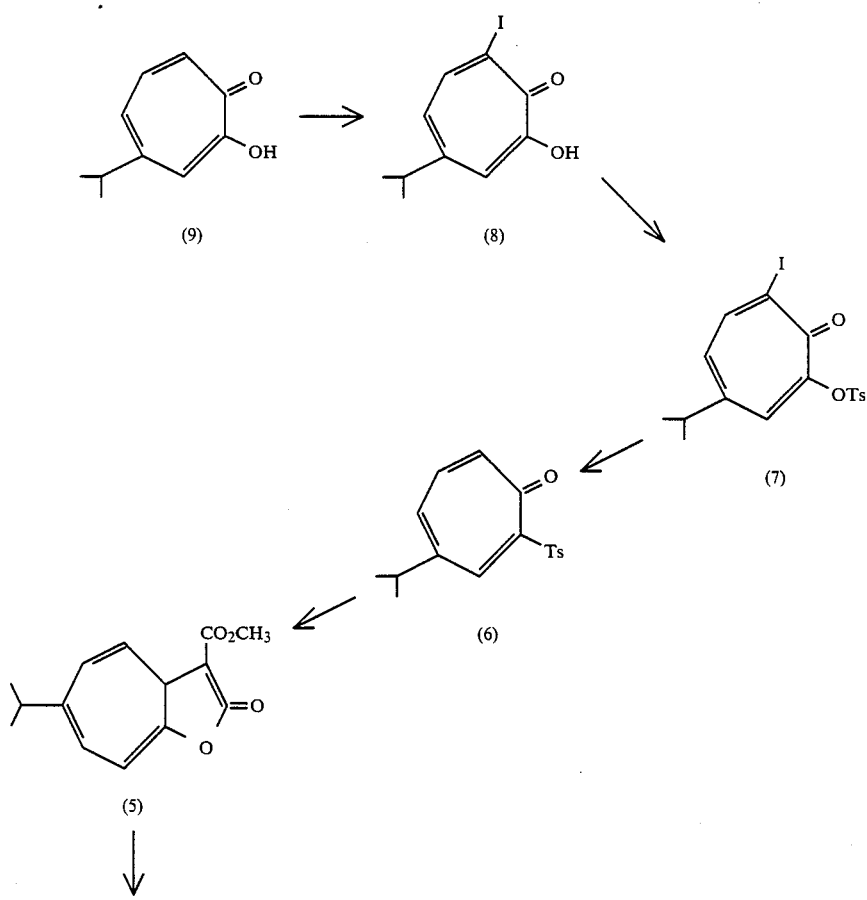

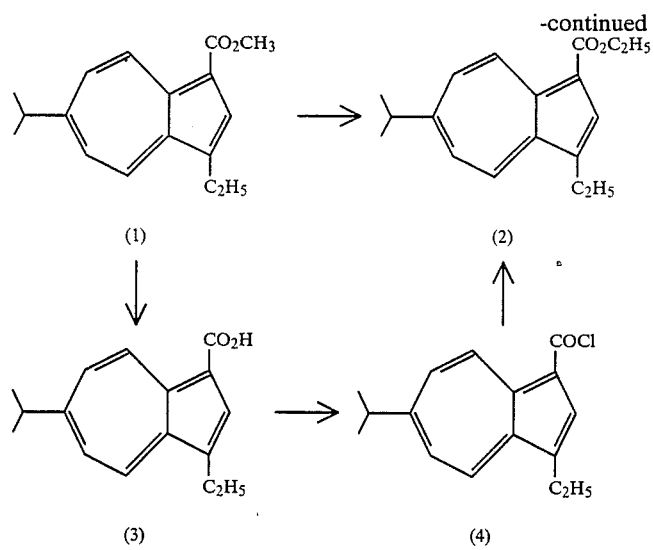

4-Isopropyl-7-iodotropolone (8) is synthesized by the iodination of hinokitiol (9) in alkaline solution. 2-Tosyloxy-4-isopropyltropone (6) is obtained by the tosylation of the product (8) in the presence of a basic catalyst, and then the reductive deiodination of the resulting tosylate (7) (See "Great Organic Chemistry: Non-Benzene-relating Aromatic Compounds", published by Asakurà Shoten in 1960, Japan).

3-Methoxycarbonyl-6-substituted 2H-cyclohepta[b]furan-2-one (5) is obtained by suspending thus obtained 2-tosyloxy-4-substituted tropone (6) in methanol, and reacting it with malonic acid dimethylester in the presence of sodium methoxide in methanol or a methanol solution of sodium hydroxide.

The product (5) is warmed in the presence of a base capable of forming an enamine with an aldehyde, such as morpholine and pyrrolidine, to form 1-methoxycarbonyl-3-substituted-6-substituted azulene (1) according to the procedure described in JP-A-126427/1982.

1-ethoxycarbonyl-3- and -6-disubstituted azulene (2) can be obtained by firstly hydrolyzing the compound (1) in aqueous alkaline solution to produce the carboxylic acid (3), which is then treated with oxalyl chloride in benzene to give the novel acid chloride (4) as an unstable oily substance. 1-Ethoxycarbonyl-3-ethyl-6-isopropylazulene (2) is then obtained by adding ethanol to the compound (4).

The azulene derivative (2) of the present invention may also be easily formed by adding sodium ethylate to the compound (1) in ethanol.

The azulene derivatives of the present invention are useful as a hypolipidemic drug for treating hyperlipidemia in mammals including humans. The derivatives can be used by formulating them into preparations such as tablets, capsules, and elixirs, for oral administration and into aseptic solutions or suspensions for parenteral administration. The azulene derivatives of the present invention can be administered to a subject necessitating such treatment (animals or humans) in a dosage range of 0.2 to 500 mg per subject, generally several times a day, that is, in a total daily dosage of 1 to 2000 mg. The dosage varies according to the seriousness of the disease, the body weight of the subject, and other factors known by those skilled in the art.

The foregoing azulene derivatives are formulated into pharmaceutical compositions stated below. About 0.2 to 500 mg of a compound of the present invention, or a mixture thereof, are blended into unit dosage forms generally acknowledged or required for pharmaceutical practice, together with for example pharmaceutically acceptable vehicles, carriers, excipients, binders, antiseptics, stabilizers and flavourings. The amount of active substance in these compositions or preparations is adjusted so as to give an appropriate dosage of the prescribed range.

Specific materials which can be incorporated into tablets, capsules, and so forth, are: binders such as tragacanth, gum arabic, cornstarch, and gelatine; excipients such as microcrystalline cellulose; swelling agents such as cornstarch, pregelatinized starch, and arginic acid; lubricants such as magnesium stearate; sweeteners such as sucrose, lactose, and saccharin; and flavourings such as peppermint, oil from Gaultheria acenothrix Maxim, and cherry. When the unit dosage form of the preparation is in the form of a capsule, a liquid carrier such as a fatty oil can further be incorporated in the foregoing materials. Various other materials can be present as coating materials or materials which vary the physical form of the unit dosage forms. For example, tablets can be coated with shellac and/or sugar. Syrups or elixirs can contain active compounds, sucrose as a sweetener, methylparaben and/or propylparaben as antiseptics, colouring matter, and flavouring such as cherry and/or an organic flavouring agent.

Aseptic compositions for injection can be formulated according to the usual practice for preparation of pharmaceutical dosage forms, in which practice an active substance is dissolved or suspended in a vehicle such as water for injection; natural vegetable oils such as sesame oil, palm oil, peanut oil, and cotton seed oil; and synthetic fat vehicles such as ethyl oleate. A buffer, an antiseptic, and an antioxidant can further be incorporated as the occasion demands.

The present invention is further explained in more detail in the following preparative and experimental examples which include the preparation and testing of the corresponding 7-substituted azulenes for purposes of comparison.

EXAMPLE 1

1-Methoxycarbonyl-3-ethyl-6-isopropylazulene (1)

(A) Synthesis of 4-isopropyl-7-iodo-tropolone (8)

Hinokitiol (50 g, 0.3 mole) (commercially available) and potassium carbonate (85 g, 0.61 mole) are dissolved in water (230 ml) and cooled. Iodine (77.3 g) and potassium iodide (83.3 g) are dissolved in water (230 ml) and the thus obtained aqueous solution is added dropwise to the cooled hinokitiol solution. It is stirred for 4 hours, and then stood overnight at room temperature. It is cooled again with ice and the precipitated crystals are filtered to give the potassium salt of the compound (8) (100.1 g, yield 100%).

(B) Synthesis of 2-tosyloxy-4-isopropyl-7-iodo-tropone (7)

The above-mentioned potassium salt of compound (8) (164 g, 0.5 mole) and tosyl chloride (209.6 g, 1.1 mole) are suspended in acetone (2 l), and the thus obtained mixture is stirred while cooling with ice. It is further stirred overnight at room temperature and then 1N potassium hydroxide aqueous solution is added dropwise thereto under cooling with ice until it shows alkaline with litmus. The reaction mixture is poured into ice-water (5 l), and the precipitated crystals are filtered, washed with water and then dried to obtain the product (7) yielding 222 g, 100%.

(C) Synthesis of 2-tosyloxy-4-isopropyl-tropone (6)

The above-mentioned compound (7) (35.5 g, 0.08 mole) and anhydrous sodium acetate (9.84 g, 0.12 mole) are dissolved in methanol (500 ml). 5% Pd-C (1.5 g) is added thereto and it is reduced catalytically by hydrogen gas. After absorption of 2.1 l of hydrogen gas, the used catalyst is removed by the filtration. Methanol is distilled off under reduced pressure, and then the remaining mixture is stirred with water (200 ml). The precipitated crystals are filtered and dried to obtain the compound (6) at a yield of 22.6 g, 98%.

(D) Synthesis of 3-methoxycarbonyl-6-isopropyl-2H-cyclohepta[b]furan-2-one (5)

2-Tosyloxy-4-isopropyl tropone (6) (477.6 g, 1.5 mole) and malonic acid dimethylester (297.2 g, 2.25 mole) are mixed with methanol (6.5 l) and then cooled to −5° C. A previously prepared methanol solution (382 ml) of sodium hydroxide (90.9 g) is added dropwise to the above cooled methanol solution. It is stirred for 5 hours, and then poured into ice-water (7.3 kg) under stirring. On filtration the compound (5) is obtained at a yield of 339.1 g, 91.8%.

(E) Synthesis of 1-methoxycarbonyl-3-ethyl-6-isopropylazulene (1)

n-Butyraldehyde (61.5 g, 0.853 mole) and morpholine (61.9 g, 0.71 mole) are added to cooled ethanol (400 ml), and then the compound (5) (68 g, 0.276 mole) is added thereto. The obtained mixture is stirred and warmed to dissolve the solid substance homogeneously. It is heated under reflux for 8 hours, and then the solvent is distilled off under reduced pressure to precipitate an oily material. The obtained oily material is dissolved in benzene (450 ml), washed twice with the same volume of water, three times with 1N HCl (400 ml), and further twice with water (400 ml). The obtained benzene solution is passed through alumina (500 g), and the eluted solution is concentrated to obtain the compound (1) at a yield of 57.4 g, 81.2%. It is recrystallized in n-hexane to give the purified product (55 g) in the purple crystalline form.

EXAMPLE 2

1-Ethoxycarbonyl-3-ethyl-6-isopropylazulene (2)

(A) Synthesis of 1-carboxy-3-ethyl-6-isopropylazulene (3)

Potassium hydroxide (328 g, 5.75 mole) is dissolved in ethanol (2.6 l) and water (0.4 l). 1-Methoxycarbonyl derivative (1) (200 g, 0.78 mole) is added thereto and dissolved at 50° C. After that, it is heated under reflux on an oil bath, cooled, and then poured into ice-water (6 kg). Concentrated hydrochloric acid (450 ml) is added dropwise to adjust the pH value to 2.0.

The precipitated crystals are filtered and washed with water, 2.5 l. It is dried at 55° C. under heating and reduced pressure to obtain the compound (3), at a yield of 188.6 g, 99.7%, having a melting point of 154° to 155.5° C.

Elementary Analysis: Found C79.57%, H7.70%. Calculated for $C_{16}H_{18}O_2$ C79.31%, H7.49%.

I.R. Spectrum (KBr, disc) 1650 cm$^{-1}$ (C=O).

Mass Spectrum: 242 (M+).

(B) Synthesis of 1-ethoxycarbonyl-3-ethyl-6-isopropylazulene

The above-mentioned azulene carboxylic acid (3) (4.84 g, 0.002 mole) is suspended in benzene (100 ml), and oxalyl chloride (2.8 g, 0.02 mole) is added dropwise thereto under cooling with ice. The mixture is stirred for 3 hours at room temperature and cooled with ice again. Ethyl alcohol (100 ml) is added dropwise thereto and stirred for 2 hours at room temperature. The mixture is poured into ice-water (300 ml) and extracted with benzene (100 ml). The benzene layer is separated, and then washed with water. The benzene solution is concentrated under reduced pressure, and n-hexane is added thereto to obtain the ethyl ester derivative (2) at a yield of 4.5 g, 83.3%, having a melting point of 48° to 49° C.

Elementary Analysis: Found C80.08%, H 8.35%. Calculated for $C_{18}H_{22}O_2$ C79.96%; H.8.20%.

I.R. Spectrum (KBr, disc) 1684 cm$^{-1}$ (C=O).

Mass Spectrum 280 (M+).

EXAMPLE 3

1-Ethoxycarbonyl-3-ethyl-6-isopropylazulene (2)

(Alternative process)

Sodium (23 g, 1 mole) is dissolved in ethanol (1 l), and 1-methoxycarbonyl-3-ethyl-6-isopropylazulene (1) (25.6 g 0.1 mole) is added thereto. It is stirred for 72 hours at room temperature, and then the alcohol solution is concentrated under reduced pressure, and poured into ice-water (1.8 kg). The pH value of the solution is adjusted to 2.0 by the addition of 6N sulfuric acid dropwise, and the mixture is extracted with chloroform (800 ml). The chloroform is distilled off under reduced pressure, and the residue is dissolved in benzene and purified by silica gel chromatography to obtain the compound (2), at a yield of 18.7 g, 69%.

EXAMPLE 4

1-Ethoxycarbonyl-3-ethyl-7-isopropylazulene

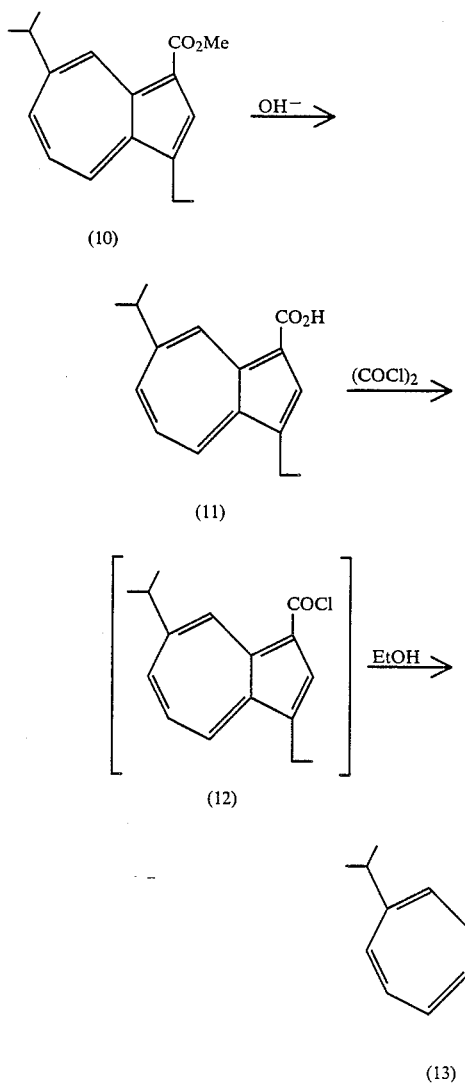

(A) Synthesis of 1-carboxy-3-ethyl-7-isopropylazulene (11)

Potassium hydroxide (16.4 g) was dissolved in a mixture of water (10 ml) and ethanol (130 ml), and the thus obtained solution was added to 1-methoxylcarbonyl-3-ethyl-7-isopropylazulene (10). It was heated under reflux for 2 hours.

After cooling, the reaction mixture was poured into ice-water (300 ml), and the thus obtained solution was made acidic while stirring by the addition of conc. hydrochloric acid. The precipitate was filtered, washed with water, and dried to give 1-carboxy-3-ethyl-7-isopropyl-azulene (11), at a yield of 9.32 g (98.6%), having a melting point of 154° to 155.5° C.

Elementary Analysis: Found, C 79.59%; H 7.68%.
Calculated for $C_{16}H_{18}O_2$, C 79.31%; H 7.49%.

I.R. Spectrum (KBr, disc) 1640 cm$^{-1}$ (C=O).
Mass Spectrum 242 (M+).

(B) Synthesis of 1-ethoxycarbonyl-3-ethyl-7-isopropylazulene (13)

The product (11) (1.21 g) was suspended in benzene (20 ml) and the mixture was stirred under cooling to 6° C. with ice-water. To the mixture was added dropwise a solution obtained by dissolving oxalyl dichloride (0.773 g) in benzene (5 ml). The mixture was stirred for 30 minutes at the same temperature as above, and then stirred for 1 hour at room temperature. The reaction solution, from which the acid chloride derivative (12) was not isolated, was added dropwise to ethanol (20 ml) under stirring and cooling with ice-water. It was kept to the same reduced temperature (6° C.) and then stirred for 1 hour at room temperature.

The reaction solution was concentrated under reduced pressure to solid form. The residue was dissolved in a small amount of benzene and passed through the alumina column (6 g). It was further purified by column chromatography with silica gel (600 g, eluting with benzene. From thus obtained benzene solution, the benzene was distilled off. The residue was recrystallized from hexane to give the product (13) in a dark purple crystalline form, at a yield of 1.13 g (83.6%), having a melting point of 58° to 60° C.

Elementary Analysis: Found, C 80.12%; H 8.04%.
Calculated for $C_{18}H_{22}O_2$, C 79.96%; H 8.20%.

I.R. Spectrum (KBr, disc) 1679 cm$^{-1}$ (C=O).
Mass Spectrum 270 (M+).

EXAMPLE 5

1-Isopropoxycarbonyl-3-ethyl-7-isopropylazulene

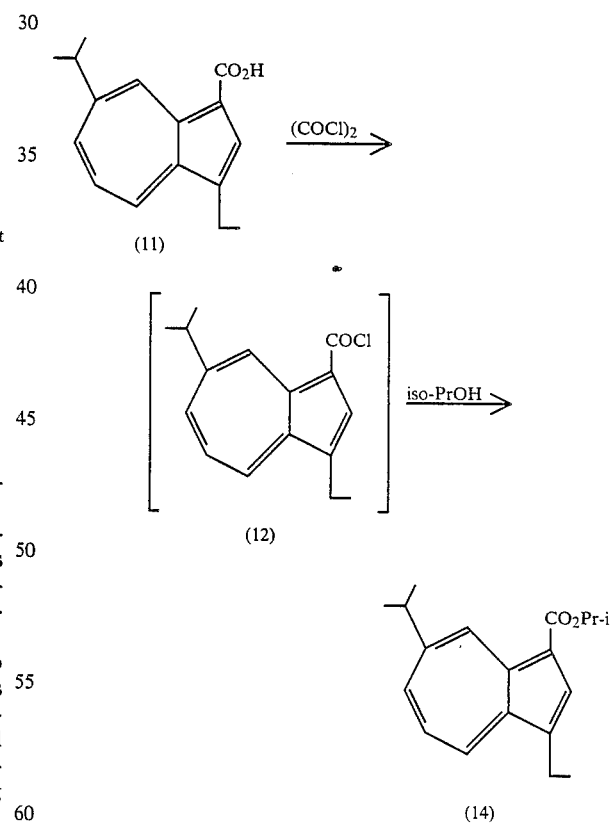

(A) Synthesis of 1-isopropoxycarbonyl-3-ethyl-7-isopropylazulene (14)

The acid chloride derivative (12) was produced in the same manner as in the synthesis of the above-mentioned 1-ethoxycarbonyl-3-ethyl-7-isoproylazulene (13) using 1-carboxy-3-ethyl-7-isopropylazulene (11) (1.21 g) as a starting material. Isopropanol was employed in place of the ethanol under the same reaction conditions and treatment as above to obtain the product (14) in a dark purple crystalline form, at a yield of 1.34 g (94.2%), having a melting point of 69° to 71° C.

Elementary Analysis: Found, C 80.46%; H 8.46%. Calculated for $C_{19}H_{24}O_2$, C 80.24%; H 8.51%.

I.R. Spectrum (KBr, disc) 1682 cm$^{-1}$ (C=O).

Mass Spectrum 284 (M+).

EXAMPLE 6

1-Isopropoxycarbonyl-3-ethyl-6-isopropylazulene

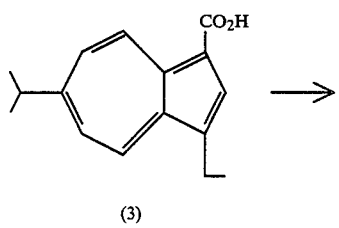

(3)

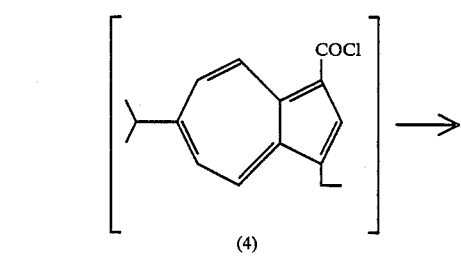

(4)

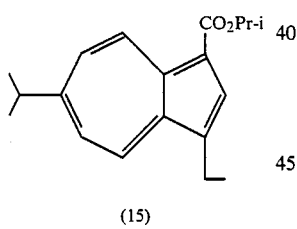

(15)

(A) Synthesis of 1-isopropoxycarbonyl-3-ethyl-6-isopropylazulene (15)

The acid chloride derivative (4) was produced in the same manner as in the synthesis of the above-mentioned 1-ethoxycarbonyl-3-ethyl-7-isopropylazulene (13) using 1-carboxy-3-ethyl-6-isopropylazulene (3) (1.45 g) as a starting material. The product (4) was not isolated. The reaction solution including product (4) was treated in the same manner as in the above-mentioned synthesis of 1-isopropoxycarbonyl-3-ethyl-7-isopropylazulene (14) to obtain a dark purple oily substance (15), at a yield of 1.42 g (83.3%).

I.R. Spectrum (KBr, tablet): 1688 cm$^{-1}$ (C=O).

Mass Spectrum 284 (M+).

EXAMPLE 7

1-Methoxycarbonyl-3-ethyl-5-isopropylazulene (23)

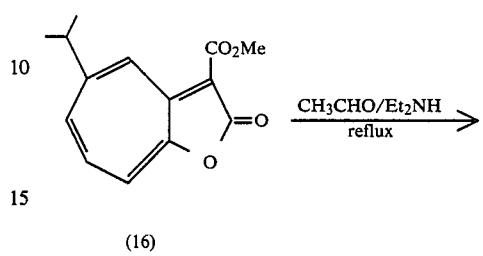

(16)

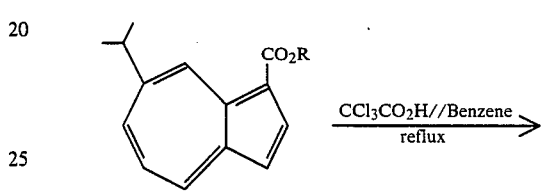

(17) R = Me
(18) R = H

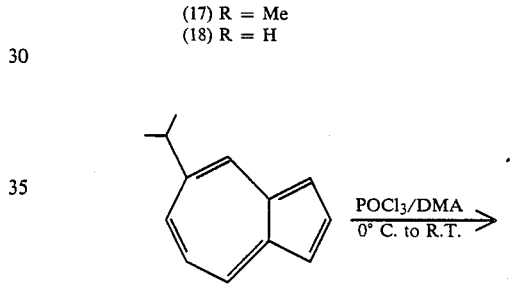

(19)

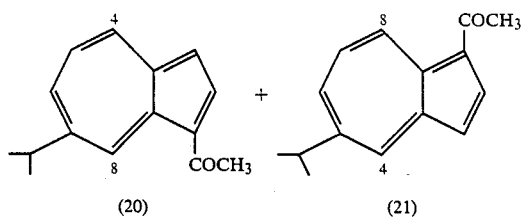

(20)          (21)

NaBH$_4$—BF$_3$
Ether/Diglyme

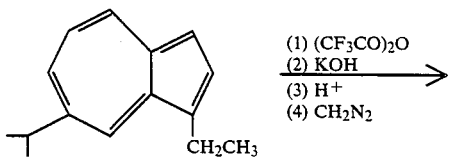

(22)

(1) (CF$_3$CO)$_2$O
(2) KOH
(3) H$^+$
(4) CH$_2$N$_2$

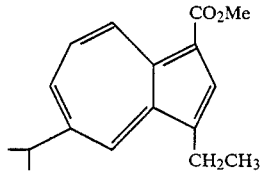

(23)

(A) Synthesis of 1-methoxycarbonyl-7-isopropylazulene (17)

To a diethylamine (120 ml) suspension of 3-methoxycarbonyl-5-isopropyl-2H-cyclohepta[b]furan-2-one (16) (5.0 g) acetaldehyde (5.7 ml) was added.

The thus obtained mixture was heated under reflux for 3 hours 20 minutes in an oil bath. The reaction solution was cooled to room temperature, and the diethylamine and acetaldehyde were distilled off under reduced pressure. The residue was dissolved in benzene, and the benzene solution was washed with water and dried. The solvent was distilled off to obtain the crude product (17).

It was purified by column chromatography on silica gel (120 g), eluting with benzene. The first eluting part gave the product (17) in a red-purple oily state, at a yield of 3.39 g (73.2%).

(B) Synthesis of 5-isopropylazulene (19)

Potassium hydroxide (10.5 g) was dissolved in a mixture of ethanol (80 ml) and water (15 ml). The compound (17) (12.43 g) was added thereto and the mixture was heated under reflux for 50 minutes in an oil bath. The reaction solution was cooled to room temperature, and then poured into water (400 ml). The solution was made acidic (pH 3) with conc. HCl. The precipitate was filtered, washed with water and dried to obtain 1-carboxy-7-isopropylazulene (18), at a yield of 2.1 g (92.3%).

The well-dried compound (18) (2.1 g) was dissolved in benzene (150 ml), and then trichloroacetic acid (0.4 g) was added. The mixture was heated under reflux for 2 hours on an oil bath. The reaction mixture was cooled to room temperature, and then passed through a column of alumina. From the eluted solution the solvent was distilled off to obtain the crude product (19), at a yield of 1.02 g. The crude product was purified on an alumina (20 g) column, eluting with hexane, to obtain the product (19) at a yield of 725 mg (91.2%) as a blue oily substance.

(C) Synthesis of 1-acetyl-7-isopropylazulene (20)

To a dimethylacetamide (80 ml) solution of the compound (19) (8.41 g), while stirring and cooling with ice, a dimethylacetamide (76 ml) solution of phosphorus oxychloride ($POCl_3$) (92 g) was added dropwise over 40 minutes. After the addition of the $POCl_3$ solution, it was further stirred for 5 hours at room temperature, and then poured into water (800 ml). The solution was made basic (pH 10) by the addition of aqueous potassium hydroxide, and was extracted 5 times with benzene. The benzene solutions were mixed, washed with water and dried. From the benzene solution, the solvent was distilled off to obtain an oily substance. It was purified by silica gel column chromatography (650 g), eluting with benzene. The second-eluted part gave 1-acetyl-7-isopropylazulene (20) (4.29 g, 41%) in a red oily state.

$^1$H-NMR ($CDCl_3$, 60 MHz), H-4: 8.27 ppm (d, J=10, 2 Hz).

The 4th-eluted part gave 1-acetyl-5-isopropylazulene (21) at a yield of 3.58 g (34.1%) in a red crystalline form.

$^1$H-NMR ($CDCl_3$, 60 MHz), H-4: 8.30 ppm (d, J=2, 2 Hz), H-8: 9.70 ppm (dm, J=10 Hz).

(D) Synthesis of 1-ethyl-7-isopropylazulene (22)

The compound (20) (1.95 g) was dissolved in a mixture of diglyme (120 ml) and ether (120 ml), and $BF_3$ etherate (2.1 ml) was added to the mixture while stirring and cooling with ice. To thus produced solution, while stirring and cooling with ice, a diglyme (8 ml) solution of $NaBH_4$ (700 mg) was added dropwise. After stirring for 30 minutes, the reaction solution was poured into 5% potassium hydroxide aqueous solution. The thus obtained solution was extracted with hexane, washed with water and dried. The solvent was distilled off, and the thus obtained crude product was purified by column chromatography with silica gel (200 g), eluting with hexane. The first eluted part gave the product (22) at a yield of 1.28 g (65.6%) as a blue oily substance.

(E) Synthesis of 1-methoxycarbonyl-3-ethyl-5-isopropylazulene (23)

To the methylene chloride (80 ml) solution of the compound (22) (2.0 g), while stirring and cooling with ice, a methylene chloride (40 ml) solution of trifluoroacetic anhydride (3.18 g) was added dropwise. After stirring for 3 hours, the reaction solution was transferred into a separating funnel, washed with water and dried. The solvent was distilled off to obtain the trifluoroacetyl compound (2.42 g, 81.4%), which was not further purified. The product was added to potassium hydroxide (0.9 g) in an ethanol (90 ml)-water (10 ml) solution, and the thus obtained solution was heated under reflux for 1.5 hours. After completion of the reaction, the reaction solution was poured into water (200 ml). The aqueous solution was adjusted to pH 3 with 6N HCl to produce a precipitate. The precipitate was filtered, washed with water, and dried to obtain the carboxylic acid derivative at a yield of 1.80 g (96%).

The carboxylic acid derivative as synthesized above, was dissolved in a mixture of chloroform (30 ml) and methanol (10 ml). An ether solution of diazomethane was added thereto while cooling with ice to produce the methylated derivative. The thus obtained product was purified by chromatography with silica gel (120 g), eluting with benzene. The second-eluted part gave the ester product (23) at a yield of 1.90 g (100%) as a reddish purple oil.

Elementary Analysis: Found, C 79.82%; H 7.73%. Calculated for $C_{17}H_{20}O_2$, C 79.65%; H 7.86%.

I.R. Spectrum ($CHCl_3$ solution) 1670 cm$^{-1}$ (C=O). Mass Spectrum 256 (M+).

EXAMPLE 8

1-methoxycarbonyl-3,6-diisopropylazulene (24)

Isovaleraldehyde (5.16 g) and morpholine (4.36 g) are added to ethanol (14 ml) and then 3-methoxycarbonyl-6-isopropyl-2H-cyclohepta[b]furan-2-one (5) (2.46 g) is added thereto. The obtained mixture is heated under reflux for 16 hours, and then the solvent is distilled off under reduced pressure to give an oily material. The obtained oily material is dissolved in toluene (20 ml), washed twice with water (20 ml) and 4 times with 1N HCl (20 ml), and further, twice with water (40 ml). The obtained toluene layer is passed through silica gel column (1.05 kg), the column is eluted with toluene. From the eluted parts including the product (24), the solvent is distilled off under reduced pressure to give the compound (24) as a purple oily material in a yield of 2.08 g, 76.%.

Elementary Analysis: Found C, 80.06%, H, 8.20%. Calculated for $C_{18}H_{22}O_2$, C, 79.96%, H, 8.20%.

I.R. Spectrum (liquid film): 1690 $cm^{-1}$.

Mass Spectrum: 270 ($M^+$).

EXPERIMENTAL EXAMPLE

Hypolipidemic effect in mice

21 Days-ICR male mice were reared for 2 days with a commercial feed, and then reared for 7 days with experimental feed containing 1% cholesterol. During this period, water and feed are supplied ad libitum.

The composition of the experimental feed is as follows.

| Feed | Percent (%) |
|---|---|
| Cane sugar | 59.79 |
| Casein | 20.0 |
| Powder of filter paper | 4.0 |
| Mixture of minerals* | 4.0 |
| Mixture of vitamins* | 1.0 |
| Choline chloride | 0.2 |
| Cholesterol | 1.0 |
| Palm oil | 5.0 |
| Soya bean Oil | 5.0 |
| Vitamin E | 0.01 |

*Oriental Yeast Industry Co., Ltd., Mr. Herber's Assorted Feed

On the 6th day and 7th day after the start of the experimental feed, the administration composition shown in Table 1 was administrated orally into the paunch by gavage.

TABLE 1

| Administration Composition | Administration of azulene derivative per 1 kg body weight | Administration Volume per 10 g body weight |
|---|---|---|
| 0.25% Sodium Carboxymethyl Cellulose | Control | 0.5 ml |
| 0.25% Sodium Carboxymethyl Cellulose + Azulene derivative (8 mg/ml) of the example 1 | 400 mg/kg | 0.5 ml |

In the above administration composition, the azulene derivative in crystalline form was powdered in a glass-mortar and then mixed with 0.25% CMC solution as shown in Table 1. After the mixing, it was suspended by supersonic frequency treatment. This suspension was made up each time just before administration.

The mice were separated into groups before the first such administration on the 6th day after the start of the experimental feed. Ten mice were assigned to each group, weighing 21.2±1.2 g on average. The mice were denied food for 16 hours after the completion of the second administration on the 7th day after the start of the experimental feed.

At the end of the abstinence period blood was taken under anaesthesis with ether, and the serum was separated by a conventional method.

The amount of the total cholesterol in the blood was determined using Hitachi 706D Type, auto-analyzer (Enzymatic Method), and the amount of the heparin precipitating betalipoproteins were determined using the same instrument (Nephelometric Method).

Changes in the value of the total cholesterol resulting from the administration composition are shown in Table 2.

TABLE 2

Decreasing Effect of Serum Cholesterol in Mouse

| Sample (Structure) | DOSE (mg/kg PO) | HYPOCHOLEST*1 (%) | HP—BETALIPO*2 (%) | HPL/ CHOL |
|---|---|---|---|---|
| [azulene with $CO_2Me$] | 400 | 78 | 86 | 0.64 |
|  | 50 | 29 | 34 | 0.93 |
|  | 25 | 22 | 32 | 0.87 |
|  | 10 | 0 | 0 |  |
| [azulene with $CO_2Et$] | 400 | 74 | 84 | 0.62 |
|  | 100 | 44 | 62 | 0.68 |
|  | 50 | 25 | 28 | 0.96 |
|  | 25 | 23 | 24 | 0.99 |
|  | 10 | 4 | 0 |  |
| [azulene with $CO_2$-iPr] | 200 | 69 | 77 | 0.74 |
|  | 100 | 50 | 60 | 0.80 |
|  | 50 | 28 | 47 | 0.74 |
|  | 25 | 9 | 8 |  |

TABLE 2-continued

Decreasing Effect of Serum Cholesterol in Mouse

| Sample (Structure) | DOSE (mg/kg PO) | HYPOCHOLEST*[1] (%) | HP—BETALIPO*[2] (%) | HPL/ CHOL |
|---|---|---|---|---|
| 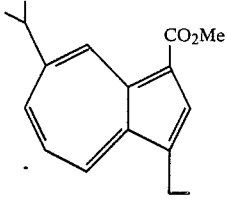 | 400<br>200<br>100<br>50 | 50<br>37<br>34<br>4 | 60<br>52<br>41<br>0 | 0.80<br>0.76<br>0.89 |
| 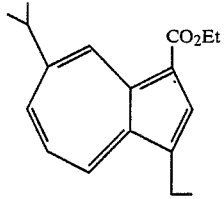 | 400<br>200<br>100<br>50 | 50<br>44<br>23<br>0 | 65<br>52<br>30<br>0 | 0.70<br>0.86<br>0.91 |
| 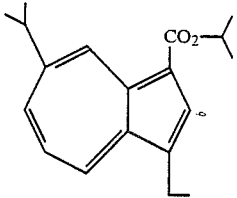 | 200<br>100<br>50 | 35<br>20<br>9 | 54<br>35<br>0 | 0.71<br>0.81 |
| 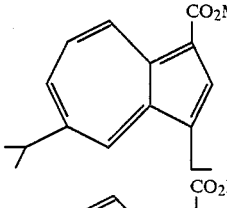 | 200<br>100<br>50<br>25 | 72<br>32<br>26<br>0 | 84<br>57<br>48<br>0 | 0.57<br>0.63<br>0.70 |
| 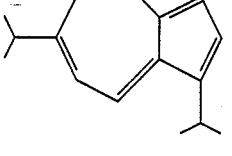 | 200<br>100<br>25<br>10 | 44<br>43<br>31<br>8 | 63<br>59<br>40<br>6 | 0.66<br>0.72<br>0.87 |
| control 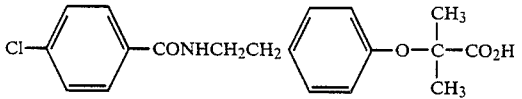<br>(Bezafibrate) | 200 | 33 | 38 | 0.93 |

*[1]Hypocholesterolemic effect
*[2]Heparin Precipitating betalipoproteins

Abnormal change in body weight of the mice was not observed with the administration of the product of the present invention, and no particular abnormal symptoms were found on post-mortem investigation.

As can be seen from table 2, a remarkable improvement is shown in cholesterol-lowering action of 1-methoxycarbonyl-3-ethyl-6-isopropylazulene (1) of the present invention as compared with the corresponding 7-isopropyl derivative (JP-A-156611/1985). Moreover, such action is maintained even though it is administered at a lower dosage.

Similarly a remarkable improvement is shown in cholesterol-lowering action in the 1-ethoxycarbonyl and 1-isopropoxycarbonyl derivatives of the present invention in comparison with the corresponding 7-substituted compound.

We claim:

1. An azulene derivative having the formula:

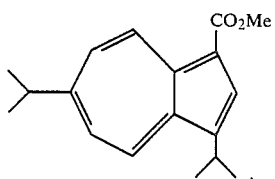

2. A method for treating hyperlipidemia in a nammal in need thereof, which comprises administering to said mammal a hypolipidemic effective dose of an azulene derivative having the formula:

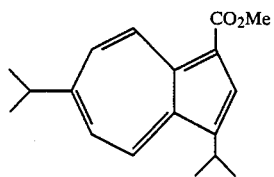

to a mammal in need of such treatment.

3. A pharmaceutical composition for treating hyperlipidemia in a mammal comprising a hypolipidemic amount of an azulene derivative having the formula:

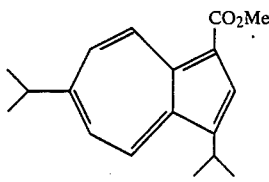

together with a pharmaceutically acceptable excipient.

4. The method according to claim 2, wherein said mammal is a human.

5. The method according to claim 3, wherein said mammal is a human.

* * * * *